US012121383B2

(12) United States Patent
Abe et al.

(10) Patent No.: US 12,121,383 B2
(45) Date of Patent: Oct. 22, 2024

(54) X-RAY DIAGNOSTIC APPARATUS AND CONTROL METHOD

(71) Applicant: Toshiba Medical Systems Corporation, Otawara (JP)

(72) Inventors: Shingo Abe, Nasushiobara (JP); Hisato Takemoto, Nasushiobara (JP); Kazuhiro Taniyama, Otawara (JP); Hidenori Yamaguchi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 240 days.

(21) Appl. No.: 15/637,331

(22) Filed: Jun. 29, 2017

(65) Prior Publication Data

US 2018/0000438 A1    Jan. 4, 2018

(30) Foreign Application Priority Data

Jun. 29, 2016    (JP) .................................. 2016-129150

(51) Int. Cl.
*A61B 6/00* (2024.01)
*A61B 6/02* (2006.01)
(Continued)

(52) U.S. Cl.
CPC ................ *A61B 6/487* (2013.01); *A61B 6/12* (2013.01); *A61B 6/544* (2013.01); *H04N 5/32* (2013.01);
(Continued)

(58) Field of Classification Search
CPC ........... A61B 6/487; A61B 6/544; A61B 6/12; A61B 6/485; A61B 6/4441; A61B 6/022; H04N 5/32
(Continued)

(56) References Cited

U.S. PATENT DOCUMENTS 3,854,049 A * 12/1974 Mistretta ................ A61B 6/482
378/62
5,432,833 A * 7/1995 Coe .......................... H05G 1/44
378/110
(Continued)

FOREIGN PATENT DOCUMENTS

JP            2-124700 U      10/1990
JP          2003-115399       4/2003
(Continued)

OTHER PUBLICATIONS

Mitchell, Erica L. and Patricia Furey. Prevention of radiation injury from medical imaging [online]. Journal of Vascular Surgery, Jan. 2011 [retrieved on Jul. 3, 2019], vol. 53, No. 1, Supplement, pp. 22S-27S. Retrieved from the Internet: [URL: see office action] [DOI: 10.1016/j.jvs.2010.05.139].*

(Continued)

*Primary Examiner* — Katherine L Fernandez
*Assistant Examiner* — Michael S Kellogg
(74) *Attorney, Agent, or Firm* — Oblon, McClelland, Maier & Neustadt, L.L.P.

(57) ABSTRACT

An X-ray diagnostic apparatus according to an embodiment includes an X-ray tube, an X-ray detector, an arm holding the X-ray tube and processing circuitry. The processing circuitry obtains body thickness information of a subject in an acquisition direction of an X-ray image at an arm position different from an arm position at a start of acquiring X-ray images. The processing circuitry sets, based on the body thickness information of the subject, acquisition condition at the start of acquiring the X-ray images. The processing circuitry starts acquiring of the X-ray images with the set acquisition condition. The processing circuitry acquires the X-ray images sequentially by rotating the arm while iteratively setting the acquisition condition by feedback control.

20 Claims, 7 Drawing Sheets

(51) Int. Cl.
*A61B 6/12* (2006.01)
*H04N 5/32* (2023.01)

(52) U.S. Cl.
CPC .............. *A61B 6/022* (2013.01); *A61B 6/4441* (2013.01); *A61B 6/485* (2013.01)

(58) Field of Classification Search
USPC ...... 600/407; 378/95, 96, 97, 101, 108, 109, 378/110, 111, 112
See application file for complete search history.

(56) References Cited

U.S. PATENT DOCUMENTS

| | | | | |
|---|---|---|---|---|
| 5,450,462 | A * | 9/1995 | Toth | A61B 6/032 |
| | | | | 378/108 |
| 2004/0141582 | A1 | 7/2004 | Ono | A61B 6/00 |
| | | | | 378/42 |
| 2007/0104317 | A1* | 5/2007 | Ohishi | A61B 6/481 |
| | | | | 378/98.12 |
| 2008/0170657 | A1* | 7/2008 | Peeters | A61B 6/4441 |
| | | | | 378/16 |
| 2013/0089176 | A1* | 4/2013 | Nabatame | A61B 6/461 |
| | | | | 378/8 |
| 2013/0142303 | A1* | 6/2013 | Goto | A61B 6/0407 |
| | | | | 378/8 |
| 2013/0208853 | A1* | 8/2013 | Uebayashi | A61B 6/545 |
| | | | | 378/19 |
| 2014/0254751 | A1* | 9/2014 | Yabugami | A61B 6/485 |
| | | | | 378/44 |
| 2014/0341350 | A1* | 11/2014 | Muroi | A61B 6/06 |
| | | | | 378/62 |
| 2016/0089102 | A1* | 3/2016 | Wang | H05G 1/36 |
| | | | | 378/62 |
| 2016/0120496 | A1* | 5/2016 | Goto | A61B 6/542 |
| | | | | 378/108 |
| 2020/0319121 | A1* | 10/2020 | Daerr | G01N 23/046 |

FOREIGN PATENT DOCUMENTS

| | | |
|---|---|---|
| JP | 2009-207683 | 9/2009 |
| JP | 2011-161091 | 8/2011 |
| JP | 2013-192750 | 9/2013 |
| JP | 2014-209965 A | 11/2014 |
| JP | 2016-87217 | 5/2016 |
| WO | WO 2006/090877 A1 | 8/2006 |

OTHER PUBLICATIONS

Japanese Office Action issued Jun. 9, 2020 in Japanese Patent Application No. 2016-129150, 5 pages.

* cited by examiner

| ⟨FRONT DIRECTION⟩<br>ENERGY: E1<br><br>TUBE VOLTAGE: kV1<br>TUBE CURRENT: mA1<br>PULSE WIDTH: ms1<br>FOCUS SIZE: Focus1<br>RADIATION DOSE: Dose1 | ⟨SIDE DIRECTION⟩<br>ENERGY: E2<br><br>TUBE VOLTAGE: kV2<br>TUBE CURRENT: mA2<br>PULSE WIDTH: ms2<br>FOCUS SIZE: Focus2<br>RADIATION DOSE: Dose2 |
|---|---|

FIG.5
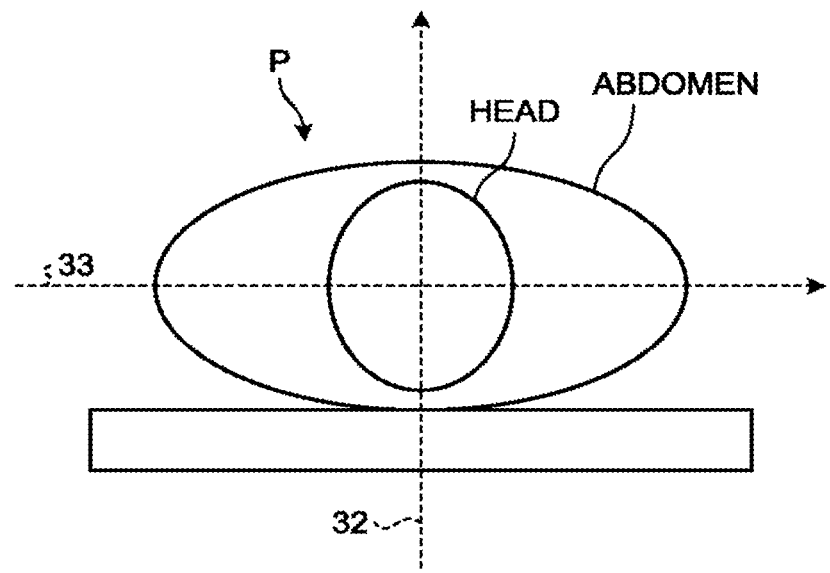
FIG.6
E1≥E2×(Dose1/Dose2) (EXAMPLE: HEAD)
TUBE VOLTAGE: HIGHkV
FOCUS SIZE: Focus2
RADIATION DOSE: Dose2
PULSE WIDTH (THIN DIRECTION): MINms
TUBE CURRENT: OPTImA
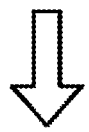
TUBE CURRENT: OPTImA
PULSE WIDTH (THICK DIRECTION): MAXms

X-RAY DIAGNOSTIC APPARATUS AND CONTROL METHOD

CROSS-REFERENCE TO RELATED APPLICATIONS

This application is based upon and claims the benefit of priority from Japanese Patent Application No. 2016-129150, filed on Jun. 29, 2016; the entire contents of which are incorporated herein by reference.

FIELD

Embodiments described herein relate generally to an X-ray diagnostic apparatus and a control method.

BACKGROUND

In X-ray diagnostic apparatuses, auto brightness control (ABC) has been known in which the brightness of X-ray images is automatically adjusted to a constant value by successively changing the X-ray conditions based on the collected X-ray images. For example, the X-ray diagnostic apparatus controls tube voltage, tube current, pulse width, and the like through feedback control by ABC during rotation imaging that collects projection data at a predetermined frame rate while rotating the C arm supporting an X-ray generator and an X-ray detector.

BRIEF DESCRIPTION OF THE DRAWINGS

FIG. 5 is a diagram illustrating an example of target sections according to the first embodiment;

FIG. 6 is a diagram for explaining an example of the setting of exposure conditions according to the first embodiment;

DETAILED DESCRIPTION

According to an embodiment, an X-ray diagnosis apparatus comprises an X-ray tube, an X-ray detector, an arm and processing circuitry. The X-ray tube is configured to radiate X-rays. The X-ray detector is configured to detect the X-rays. The arm holds the X-ray tube. The processing circuitry is configured to obtain body thickness information of a subject in an acquisition direction of an X-ray image at an arm position different from an arm position at a start of acquiring X-ray images. The processing circuitry is configured to set, based on the body thickness information of the subject, acquisition condition at the start of acquiring the X-ray images. The processing circuitry is configured to start acquiring of the X-ray images with the set acquisition condition. The processing circuitry is configured to acquire the X-ray images sequentially by rotating the arm while iteratively setting the acquisition condition by feedback control.

Embodiments of an X-ray diagnostic apparatus will be described in detail below with reference to the accompanying drawings. It should be noted that the X-ray diagnostic apparatus according to the subject application is not limited to the following embodiments.

First Embodiment

Figure 1:
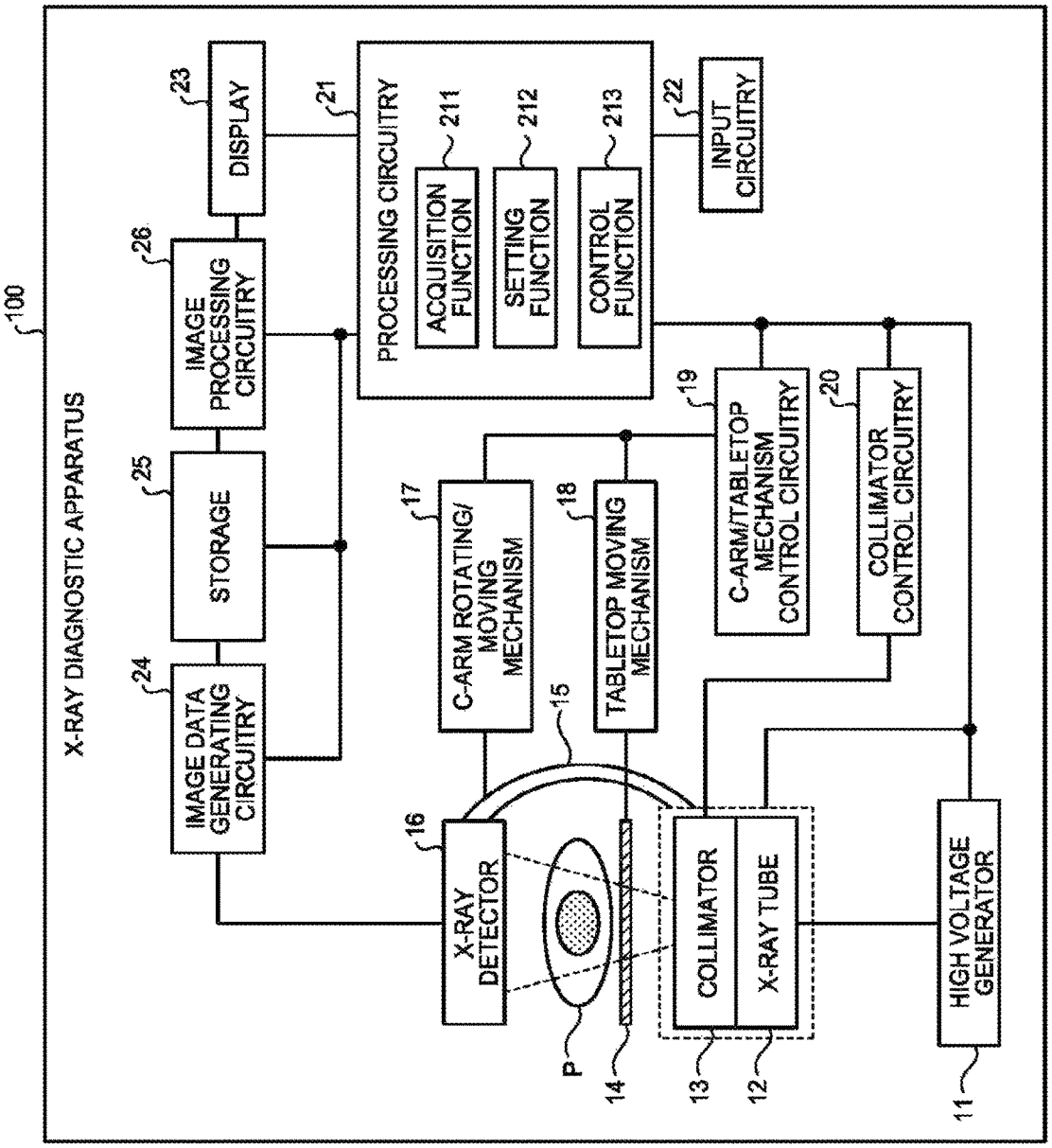
FIG. 1 is a diagram illustrating an example of the configuration of an X-ray diagnostic apparatus according to a first embodiment.

First, the overall configuration of an X-ray diagnostic apparatus according to a first embodiment will be described. FIG. 1 is a diagram illustrating an exemplary configuration of an X-ray diagnostic apparatus 100 according to the first embodiment. As illustrated in FIG. 1, the X-ray diagnostic apparatus 100 according to the first embodiment includes a high voltage generator 11, an X-ray tube 12, a collimator 13, a tabletop 14, a C-arm 15, an X-ray detector 16, a C-arm rotating/moving mechanism 17, a tabletop moving mechanism 18, C-arm/tabletop mechanism control circuitry 19, collimator control circuitry 20, processing circuitry 21, input circuitry 22, a display 23, image data generating circuitry 24, a storage 25, and image processing circuitry 26.

In the X-ray diagnostic apparatus 100 illustrated in FIG. 1, each processing function is stored in the storage 25 in the form of a computer program executable by a computer. The C-arm/tabletop mechanism control circuitry 19, the collimator control circuitry 20, the processing circuitry 21, the image data generating circuitry 24, and the image processing circuitry 26 are a processor that reads a computer program from the storage 25 and executes the computer program to implement the function corresponding to the computer program. In other words, each circuit in a state in which a computer program is read has the function corresponding to the read computer program.

The term "processor" used in the description above means, for example, a central processing unit (CPU), a graphics processing unit (GPU), or a circuit such as an application specific integrated circuit (ASIC) and a programmable logic device (for example, simple programmable logic device (SPLD), complex programmable logic device (CPLD), and a field programmable gate array (FPGA)). The processor reads and executes a computer program stored in the storage circuit to implement the function. The computer program may be directly built in a circuit in the processor, rather than being stored in a storage circuit. In this case, the processor implements the function by reading and executing the computer program built in the circuit. Each processor in the present embodiment may not be configured as a single circuit, but a plurality of independent circuits may be combined into a single processor, which implements the function.

The high voltage generator 11 generates high voltage and supplies the generated high voltage to the X-ray tube 12, under control by the processing circuitry 21. The X-ray tube 12 generates X-rays using the high voltage supplied from the high voltage generator 11.

The collimator 13 narrows X-rays produced by the X-ray tube 12 such that the X-rays are selectively applied to a region of interest of a subject P, under control by the collimator control circuitry 20. For example, the collimator 13 has four slidable collimator blades. The collimator 13 allows these collimator blades to slide under control by the collimator control circuitry 20 and thereby narrows the X-rays produced by the X-ray tube 12 to apply the narrowed X-rays to the subject P. The collimator 13 also includes an additional filter for adjusting the radiation quality. The additional filter is set, for example, depending on tests. The tabletop 14 is a bed on which the subject P lies and is disposed on a not-illustrated table (couch). The subject P is not included in the X-ray diagnostic apparatus 100.

The X-ray detector 16 detects X-rays transmitted through the subject P. For example, the X-ray detector 16 includes detecting elements arranged in a matrix. Each detecting element convert X-rays transmitted through the subject P into an electrical signal, accumulates the electrical signals, and transmits the accumulated electrical signals to the image data generating circuitry 24.

The C-arm 15 holds the X-ray tube 12, the collimator 13, and the X-ray detector 16. The C-arm 15 is rotated fast like a propeller around the subject P lying on the tabletop 14, by a motor provided at a support (not illustrated). Here, the C-arm 15 is rotatably supported with respect to three axes orthogonal to each other, namely, the XYZ axes, and is rotated individually in each axis by a not-illustrated driver. The X-ray tube 12 and the collimator 13 are disposed to be opposed to the X-ray detector 16 by means of the C-arm 15 with the subject P interposed. Although the X-ray diagnostic apparatus 100 is a single-plane system by way of example in FIG. 1, embodiments are not limited thereto and may employ a biplane system.

The C-arm rotating/moving mechanism 17 is a mechanism for rotating and moving the C-arm 15. The C-arm rotating/moving mechanism 17 can also change a source image receptor distance (SID) which is the distance between the X-ray tube 12 and the X-ray detector 16. The C-arm rotating/moving mechanism 17 can so rotate the X-ray detector 16 held by the C-arm 15. The tabletop moving mechanism 18 is a mechanism for moving the tabletop 14.

The C-arm/tabletop mechanism control circuitry 19 controls the C-arm rotating/moving mechanism 17 and the tabletop moving mechanism 18 under control by the processing circuitry 21 to adjust the rotation and movement of the C-arm 15 and the movement of the tabletop 14. For example, the C-arm/tabletop mechanism control circuitry 19 controls rotation imaging to collect projection data at a predetermined frame rate while rotating the C-arm 15, under control by the processing circuitry 21. The collimator control circuitry 20 controls the radiation range of X-rays applied to the subject P by adjusting the aperture of the collimator blades of the collimator 13, under control by the processing circuitry 21.

The image data generating circuitry 24 generates projection data using the electrical signal obtained through conversion of X-rays by the X-ray detector 16 and stores the generated projection data into the storage 25. For example, the image data generating circuitry 24 performs current-voltage conversion, analog-digital (A/D) conversion, and parallel-serial conversion on the electrical signal received from the X-ray detector 16 to generate projection data. The image data generating circuitry 24 then stores the generated projection data into the storage 25.

The storage 25 accepts and stores the projection data generated by the image data generating circuitry 24. The storage 25 stores computer programs corresponding to various functions to be read and executed by the circuits illustrated in FIG. 1. As an example, the storage 25 stores a computer program corresponding to an acquisition function 211, computer program corresponding to a setting function 212, and a computer program corresponding to a control function 213 to be read and executed by the processing circuitry 21.

The image processing circuitry 26 performs various image processing on the projection data stored in the storage 25 to generate an X-ray image, under control by the processing circuitry 21 described later. Alternatively, the image processing circuitry 26 directly acquires projection data from the image data generating circuitry 24 and performs various image processing on the acquired projection data to generate an X-ray image, under control by the processing circuitry 21 described later. The image processing circuitry 26 may store the processed X-ray image into the storage 25. For example, the image processing circuitry 26 can execute various processing with image processing filters such as moving average (smoothing) filter, Gaussian filter, median filter, recursive filter, and bandpass filter.

The image processing circuitry 26 also forms reconstruction data (volume data) from projection data collected by rotation imaging. The image processing circuitry 26 then stores the reconstructed volume data into the storage 25. The image processing circuitry 26 generates a three-dimensional image from volume data. For example, the image processing circuitry 26 generates a volume rendering image or a multi planar reconstruction (MPR) image from volume data. The image processing circuitry 26 then stores the generated three-dimensional image into the storage 25. It is noted that the image processing circuitry 26 is an example of the reconstruction circuitry in the claims.

The input circuitry 22 is implemented by, for example, a trackball, a switch button, a mouse, and a keyboard for setting a predetermined region (for example, a region of interest such as a section concerned), and a footswitch for emitting X-rays. The input circuitry 22 is connected to the processing circuitry 21 and converts an input operation accepted from the operator into an electrical signal for output to the processing circuitry 21. The display 23 displays a graphical user interface (GUI) for accepting the operator's instruction and a variety of images generated by the image processing circuitry 26.

The processing circuitry 21 controls the operation of the entire X-ray diagnostic apparatus 100. Specifically, the processing circuitry 21 executes various processing by reading a computer program corresponding to the control function 213 for controlling the entire apparatus from the storage 25 for execution. For example, the control function 213 controls an X-ray radiation dose to be applied to the subject P and ON/OFF by controlling the high voltage generator 11 in accordance with the operator's instruction forwarded from the input circuitry 22 and adjusting the voltage supplied to the X-ray tube 12. For example, the control function 213 controls the C-arm/tabletop mechanism control circuitry 19 in accordance with the operator's instruction and adjusts the rotation and movement of the arm 15 and the movement of the tabletop 14. For example, the control function 213 controls the radiation range of X-rays applied to the subject P by controlling the collimator control circuitry 20 in accordance with the operator's instruction and adjusting the aperture of the collimator blades of the collimator 13.

The control function 213 also controls, for example, the image data generation processing by the image data generating circuitry 24 and the image processing or the analysis processing by the image processing circuitry 26 in accordance with the operator's instruction. The control function 213 also performs control such that a GUI for accepting the operator's instruction or an image stored in the storage 25 appears on the display 23. The control function 213 also executes auto brightness control (ABC). For example, the control function 213 compares a preset threshold of brightness with a statistical value (average value, intermediate value, and the like) of brightness (pixel value) in the collected X-ray images and successively sets the exposure conditions (tube voltage kV, tube current mA, pulse width ms, and others) based on the comparison result. Here, the control function 213 according to the first embodiment executes feedback control of pulse width by ABC during rotation imaging. This point will be detailed later.

As illustrated in FIG. 1, the processing circuitry 21 according to the first embodiment executes the control function 213 described above as well as the acquisition function 211 and the setting function 212, which will be detailed later. It is noted that the processing circuitry 21 is an example of the processing circuitry in the claims.

The overall configuration of the X-ray diagnostic apparatus 100 has been described above. With such a configuration, the X-ray diagnostic apparatus 100 according to the present embodiment can improve the image quality in rotation imaging. Specifically, in rotation imaging intended for three-dimensional reconstruction, the X-ray diagnostic apparatus 100 ensures a maximum range of pulse widths adaptive to a body thickness change of a subject during rotation imaging and determines appropriate exposure conditions at the imaging start position according to the shape of the subject, thereby improving the image quality in rotation imaging.

Figure 2:
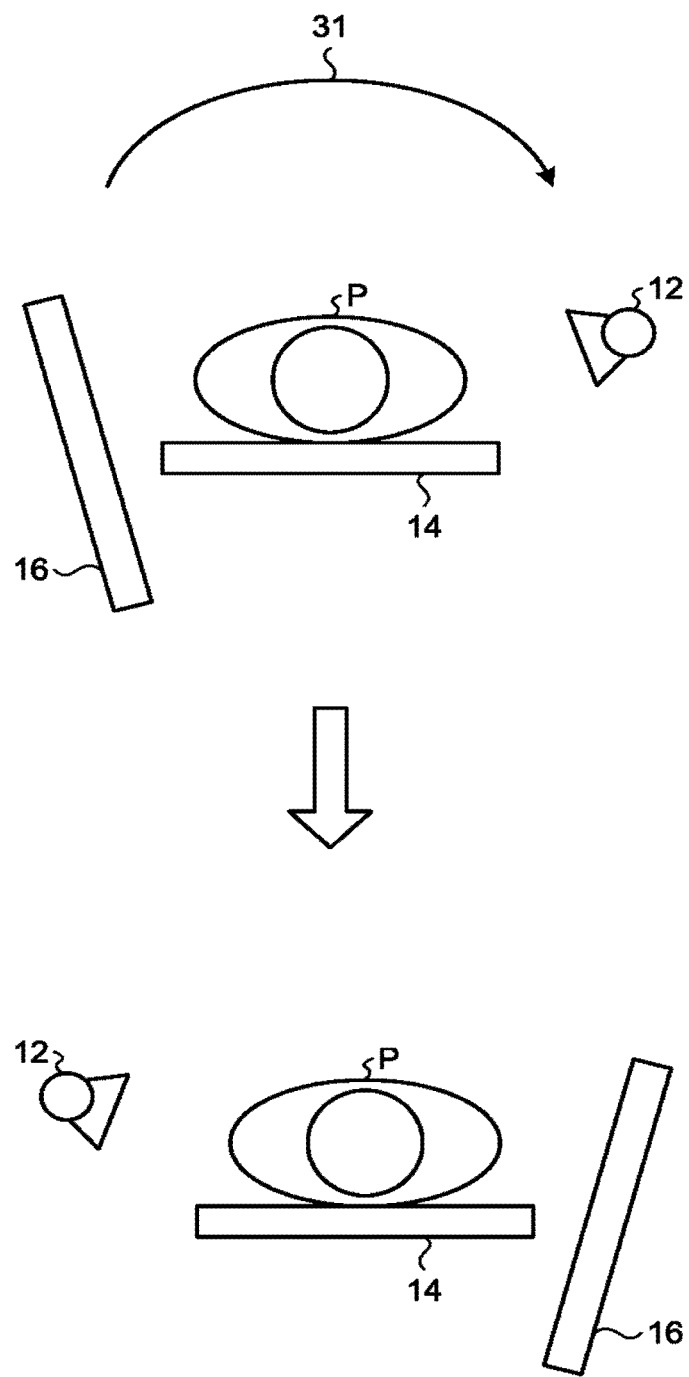
FIG. 2 is a diagram for explaining an overview according to the first embodiment.

Here, an overview of the present embodiment will be described with reference to FIG. 2. FIG. 2 is a diagram for explaining an overview according to the first embodiment. FIG. 2 illustrates rotation imaging intended for three-dimensional reconstruction as viewed from the head. In rotation imaging intended for three-dimensional reconstruction, projection data is collected in each direction over about 200° around the subject, and volume data is reconstructed through reconstruction processing using the collected projection data. In rotation imaging intended for three-dimensional reconstruction, for example, as illustrated in FIG. 2, while the arm holding the X-ray tube 12 and the X-ray detector 16 is rotated 200° in the direction indicated by an arrow 31, projection data is collected at a predetermined frame rate, and volume data is reconstructed using the collected projection data.

Here, in the X-ray diagnostic apparatus 100 according to the first embodiment, the pulse width of X-rays is successively set in ABC using the X-ray images sequentially collected during rotation imaging. In doing so, the X-ray diagnostic apparatus 100 first makes the setting so as to ensure the setting extent (range) of pulse widths to the maximum based on the body thickness information of a subject. As illustrated in FIG. 2, when rotation imaging is performed, X-rays are applied to the subject from directions in which body thickness varies, to collect projection data. Here, the body thickness varies among subjects, and the body thickness change in each direction also varies among subject Therefore, when the pulse width is successively set according to such a body thickness change, the setting of pulse width may exceed the upper limit of the apparatus for some subjects. In addition, in rotation imaging, since the C-arm 15 is driven fast, there is a limit in the range of operative pulse widths, and collection with the optimum pulse width is sometimes impossible.

The X-ray diagnostic apparatus 100 then acquires body thickness information of the subject and makes the setting so as to ensure the range of pulse widths to the maximum based on the acquired body thickness information. The X-ray diagnostic apparatus 100 then sets the pulse width at the tart of rotation imaging according to the body thickness at the start of imaging and executes feedback control of pulse width during rotation imaging within the set range. This processing keeps the brightness value as constant as possible in projection data collected from each direction and improves the image quality of the X-ray image generated from volume data reconstructed based on the projection data.

An example of the processing by the X-ray diagnostic apparatus 100 according to the first embodiment will be described below. In the following explanation, the exposure conditions of rotation imaging are set based on the exposure conditions of fluoroscopic images collected in advance.

The acquisition function 211 according to the first embodiment acquires body thickness information of a subject. Specifically, the acquisition function 211 acquires body thickness information of a subject in a direction corresponding to a position of the arm different from the position of the arm at which collection of X-ray images is started. That is, the acquisition function 211 acquires body thickness information at least at an arm position different from the arm position at the start of collection of X-ray images. For example, the acquisition function 211 estimates the respective exposure conditions in imaging from two directions in which the body thickness is different, based on the exposure conditions of fluoroscopic images collected from two directions in which the body thickness is different, and acquires body thickness information of the subject based on the estimated exposure conditions. In rotation imaging intended for three-dimensional reconstruction, since the target section is disposed near the center (isocenter) of rotation of the C-arm 15, fluoroscopic images are usually collected from two directions to perform position adjustment. Therefore, the acquisition function 211 uses the fluoroscopic images for aligning the target section with the isocenter to acquire body thickness information of the subject, for example.

Figures 3, 4:
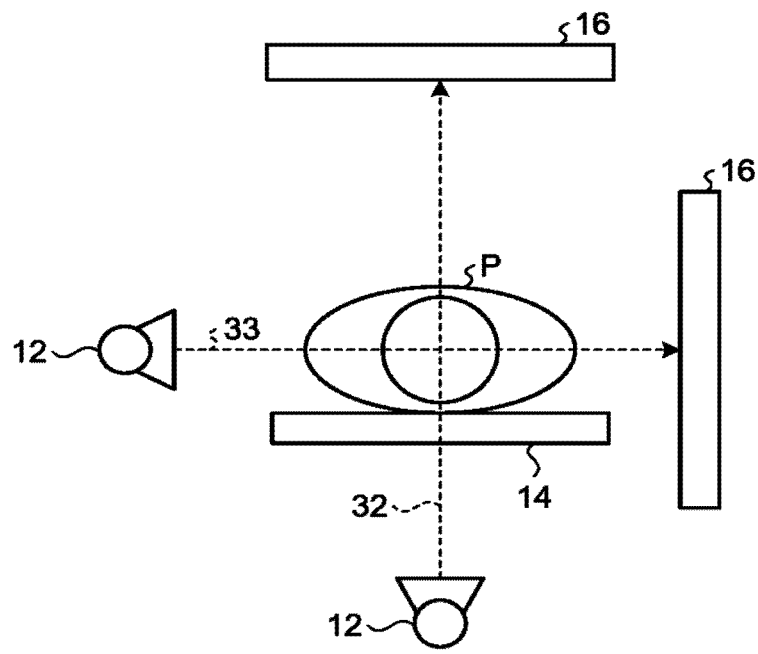
FIG. 3 is a diagram illustrating an example of collection of fluoroscopic images for position adjustment according to the first embodiment.
FIG. 4 is a diagram for explaining an example of estimation of exposure conditions in imaging by an acquisition function according to the first embodiment.

FIG. 3 is a diagram illustrating an example of collection of fluoroscopic images for position adjustment according to the first embodiment. For example, fluoroscopic images for position adjustment in rotation imaging are collected from the front direction in which X-rays are applied to the subject P from the direction indicated by an arrow 32 and the side direction in which X-rays are applied to the subject P from the direction indicated by an arrow 33, as illustrated in FIG. 3. The acquisition function 211 then calculates energy necessary for imaging in each of the front direction and the side direction, from the exposure conditions under which these fluoroscopic images are collected, and estimates the exposure conditions at the time of imaging, based on the calculated energy. The acquisition function 211 then estimates the body thickness of the subject from the calculated energy and the estimated exposure conditions.

FIG. 4 is a diagram for explaining an example of estimation of exposure conditions in imaging by the acquisition function 211 according to the first embodiment. FIG. 4 illustrates an example in which the energy at the time of imaging is calculated from the exposure conditions of fluoroscopic images, and the exposure conditions at the time of imaging are estimated, for each of the front direction (the direction of the arrow 32 in FIG. 3) and the side direction (the direction of the arrow 33 in FIG. 3). For example, as illustrated in FIG. 4, the acquisition function 211 calculates energy "E1" required for imaging from the front direction based on the exposure conditions of the fluoroscopic images collected from the front direction. The acquisition function 211 then estimates "tube voltage: kV1, tube current: mA1, pulse width: ms1, focus size: Focus1, radiation dose: Dose1", as the setting of the exposure conditions for satisfying the calculated energy "E1".

Similarly, for example, as illustrated in FIG. 4, the acquisition function 211 calculates energy "E2" necessary for imaging from the side direction, based on the exposure conditions of the fluoroscopic images collected from the side direction. The acquisition function 211 then estimates "tube voltage: kV2, tube current: mA2, pulse width: ms2, focus size: Focus2, radiation dose: Dose2", as the setting of the exposure conditions for satisfying the calculated energy "E2".

Furthermore, the acquisition function 211 compares the magnitudes of the calculated energies to estimate the body thickness of the subject. For example, the acquisition function 211 compares energy "E1" in the front direction with energy "E2" in the side direction and estimates that the body thickness in the direction with the greater energy is thick. Here, the acquisition function ill compares the energies, considering the radiation dose (the radiation dose of X-rays incident on the X-ray detector 16) in the estimated exposure conditions. That is, when the set radiation doses are identical, the magnitude of energy reflects the thickness of body thickness, whereas when the set radiation doses are different, the magnitude of energy does not reflect the thickness dy thickness alone. The acquisition function 211 therefore compares the energies, considering the condition of the radiation dose estimated in each direction.

For example, when energy "E1" is compared with energy "E2", the acquisition function 211 makes a comparison considering the radiation dose condition, by comparing "E1" with "E2×(Dose1/Dose2)". The foregoing example is provided only by way of illustration, and when energy "E1" is compared with energy "E2", "E1×(Dose2/Dose1)" may be compared with "E2".

The acquisition function 211 then estimates the body thicknesses in the front direction and the side direction, based on the comparison result between "E1" and "E2×(Dose1/Dose2)". For example, when "E1≥E2×(Dose1/Dose2)", the acquisition function 211 estimates that the body thickness in the front direction is thick and the body thickness in the side direction is thin. For example, when "E1<E2×(Dose1/Dose2)", the acquisition function 211 estimates that the body thickness in the front direction is thin and the body thickness in the side direction is thick.

In rotation imaging intended for three-dimensional reconstruction, head and abdomen are main target sections. These sections differ in direction in which the body thickness increases. FIG. 5 is a diagram illustrating an example of the target section according to the first embodiment. As illustrated in FIG. 5 for example, the head has a thicker body thickness in the front direction indicated by the arrow 32 than in the side direction indicated by the arrow 33. On the other hand, as illustrated in FIG. 5 for example, the abdomen has a thinner body thickness in the front direction indicated by the arrow 32 than in the side direction indicated by the arrow 33.

The acquisition function 211 then may identify a section based on the comparison between "E1" and "E2×(Dose1/Dose2)". For example, when "E1≥E2×(Dose1/Dose2)", the acquisition function 211 determines that the target section in rotation imaging is head. For example, when "E1<E2×(Dose1/Dose2)", the acquisition function 211 determines that the target section in rotation imaging is abdomen. When "E1<E2×(Dose1/Dose2)", it may be determined that the target section in rotation imaging is chest.

Returning to FIG. 1, the setting function 212 sets the exposure conditions at the start of collection of X-ray images, based on the body thickness information of the subject. Specifically, the setting function 212 sets the range of exposure conditions of X-ray images in feedback control and the exposure conditions at the start of collection, based on the body thickness information of the subject. More specifically, the setting function 212 sets the range of pulse widths such that the pulse width of X-rays emitted in the direction in which the body thickness of the subject is thin is reduced, and sets the pulse width included in the exposure conditions at the start of collection of X-ray images to the pulse width according to the body thickness of the subject at the start of collection. Here, the setting function 212 sets the exposure conditions of X-ray images including tube voltage, tube current, focus size, and radiation dose to values according to at least one of the section to be irradiated with X-rays and the body thickness, and also sets the range of pulse widths.

For example, the setting function 212 sets the exposure conditions including tube voltage, tube current, focus size, and radiation dose, based on the exposure conditions in imaging from two directions in which the body thickness is different and the body thickness information, and sets the range of pulse width and the pulse width at the start of collection of X-ray images. That is, the setting function 212 sets the exposure conditions other than pulse width, based on the exposure conditions estimated by the acquisition function 211, and sets the range of pulse widths and the pulse width at the start of imaging. For example, for tube voltage, focus size, and radiation dose in rotation imaging, the setting function 212 employs and sets one of the values included in the exposure conditions in two directions estimated by the acquisition function 211. Here, the setting function 212 sets the exposure conditions other than pulse width, based on at least one of the target section and the body thickness and so as to ensure the pulse width to the maximum.

For example, for the focus size included in the respective exposure conditions estimated for imaging from two directions in which the body thickness is different, the setting function 212 selects and sets a focus size according to the section to be irradiated with X-rays. As an example, when the target section is head, the setting function 212 selects and sets the focus size for the direction in which the body thickness is thin, in order to ensure spatial resolution. For example, when the body thickness is thick, a large focus size is set in order to ensure a radiation dose. When the focus size is large, however, spatial resolution decreases because defocusing occurs. The setting function 212 thus ensures spatial resolution by setting the focus size for the direction in which the body thickness is thin. That is, given that the head has a body thickness thinner in the side direction than in the front direction, the setting function 212 employs the focus size in the exposure conditions for the side direction.

On the other hand, when the target section is abdomen, the setting function 212 selects and sets the focus size for the direction in which t body thickness is thick, in order to ensure a radiation dose as much as possible. That is, given that the abdomen has a body thickness thicker in the side direction than in the front direction, the setting function 212 employs the focus size in the exposure conditions for the side direction. As described above, for the setting of focus size, the setting function 212 employs the focus size in the exposure conditions for the side direction in either case.

For example, the setting function 212 selects and sets a higher tube voltage, in the respective exposure conditions estimated for imaging from two directions in which the body thickness is different. That is, in order to ensure the range of pulse widths as wide as possible, the setting function 212 sets a higher tube voltage "HIGHkV" in the respective exposure conditions estimated for imaging from two directions, irrespective of the body thickness of the subject.

For example, the setting function 212 selects and sets a radiation dose in the direction in which the body thickness is thin, in the respective exposure conditions estimated for imaging from two directions in which the body thickness is different. That is, the setting function 212 employs the exposure conditions for the direction in which the body thickness is thin, in order to ensure a radiation dose as high as possible.

As described above, upon setting tube voltage, focus size, and radiation dose, the setting function 212 calculates and sets tube current so as to ensure the pulse width to the maximum. Specifically, the setting function 212 calculates tube current in a case where the minimum pulse width in the direction in which the body thickness is thin is set. Here, when the calculated tube current fails to be ensured by OLP (exceeds the upper limit of the apparatus), the setting function 212 reduces tube current to a value that can be ensured by OLP and increases the pulse width accordingly. In this manner, the setting function 212 sets a smallest possible pulse width "MINms" for the pulse width for the direction in which the body thickness is thin. The setting function 212 then sets the tube current at the time when the pulse width "MiNms" is set, as the optimum tube current "OPTImA" in rotation imaging.

Then, upon setting the tube current "OPTImA" the setting function 212 calculates the maximum pulse width required in the direction in which the body thickness is thick. Here, when the calculated pulse width fails to be ensured by OLP, the setting function 212 reduces the pulse width to the maximum one that can be ensured by OLP. In this way, the setting function 212 sets a largest possible pulse width "MAXms" for the pulse width in the direction in which the body thickness is thick.

As described above, while setting the focus size and the radiation dose to values according to the section or the body thickness, the setting function 212 sets a high tube voltage to set a wide range of pulse widths to the maximum, and sets tube current and pulse width so as to ensure a widest possible range within the set range. This processing allows the pulse width to further follow a body thickness change and enables reconstruction of volume data from more uniform projection data in which difference in image quality is minimized among projection data in each direction collected during rotation imaging, thereby improving the image quality in rotation imaging.

Figure 7:
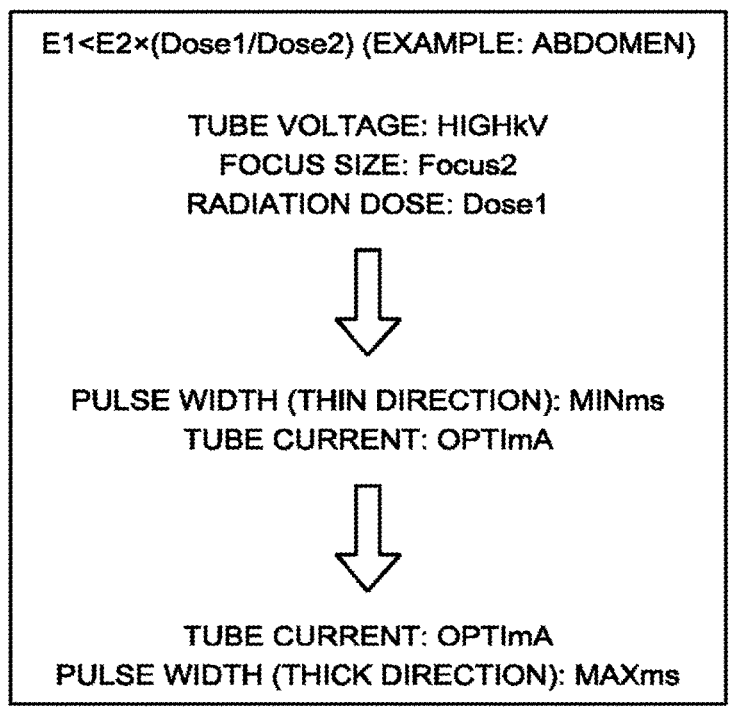
FIG. 7 is a diagram for explaining an example of the setting of exposure conditions according to the first embodiment.

An example of the setting of exposure conditions in rotation imaging will be described below with reference to FIG. 6 and FIG. 7. FIG. 6 and FIG. 7 are diagrams for explaining an example of the setting of exposure conditions according to the first embodiment. In FIG. 6 and FIG. 7, the exposure conditions in rotation imaging are set using the body thickness and the exposure conditions estimated by the acquisition function 211. FIG. 6 illustrates the setting in a case where the body thickness in the front direction is thicker than in the side direction, and FIG. 7 illustrates setting in a case where the body thickness in the front direction is thinner than in the side direction.

For example, when the body thickness in the front direction is thicker than in the side direction (when $E1 \geq E2 \times (Dose1/Dose2)$), the setting function 212 sets a high tube voltage, sets the focus size in the side direction, and sets the radiation dose in the direction in which the body thickness is thin (the side direction), as described above. That is, as illustrated in FIG. 6, the setting function 212 sets the tube voltage to "HIGHkV", sets the focus size to "Focus2", which is the focus size in the side direction, and sets the radiation dose to "Dose2", which is the radiation dose in the side direction (see FIG. 4).

The setting function 212 then sets the pulse width in the direction in which the body thickness is thin (the side direction) to the minimum value and calculates the tube current at that time. Here, when the calculated tube current can be ensured by OLP, the setting function 212 sets the set pulse width to the pulse width "MINms" for the thin direction and sets the tube current at that time as "OPTImA". On the other hand, when the calculated tube current fails to be ensured by OLP, the setting function 212 sets the pulse width "MINms" for the thin direction and the tube current "OPTImA" at that time by reducing the tube current and increasing the pulse width.

The setting function 212 then calculates the maximum pulse width required for the direction in which the body thickness is thick (the front direction) when the tube current "OPTImA" is set. Here, when the calculated pulse width can be ensured by OLP, the setting function 212 sets the set pulse width to the pulse width "MAXms" for the thick direction. On the other hand, when the calculated pulse width fails to be ensured by OLP, the setting function 212 reduces the pulse width to the one that can be ensured by OLP and sets the pulse width "MAXms" for the thick direction. That is, the setting function 212 sets the range of pulse widths from the pulse width "MINms" to "MAXms". The setting described above is executed in rotation imaging in which, for example, head is the target section.

For example, also when the body thickness in the front direction is thinner than in the side direction (when $E1 < E2 \times (Dose1/Dose2)$), the setting function 212 sets a high tube voltage, sets the focus size in the side direction, and sets the radiation dose for the direction in which the body thickness is thin (the front direction), as described above. That is, as illustrated in FIG. 7, the setting function 212 sets the tube voltage to "HIGHkV", sets the focus size to "Focus2", which is the focus size for the side direction, and sets the radiation dose to "Dose1", which is the radiation dose in the front direction (see FIG. 4).

The setting function 212 then sets the pulse width for the direction in which the body thickness is thin (the front direction) to the minimum value and calculates the tube current at that time. Here, when the calculated tube current can be ensured by OLP, the setting function 212 sets the set pulse width as the pulse width "MINms" for the thin direction and sets the tube current at that time as "OPTImA". On the other hand, when the calculated tube current fails to be ensured by OLP, the setting function 212 sets the pulse width "MINms" for the thin direction and the tube current "OPTImA" at that time by reducing the tube current and increasing the pulse width.

The setting function 212 then calculates the maximum pulse width required for the direction in which the body thickness is thick (the side direction) when the tube current "OPTImA" is set. Here, when the calculated pulse width can be ensured by OLP, the setting function 212 sets the set pulse width as the pulse width "MAXms" for the thick direction. On the other hand, when the calculated pulse width fails to be ensured by OLP, the setting function 212 reduces the pulse width to the one that can be ensured by OLP and sets the pulse width "MAXms" for the thick direction. That is, the setting function 212 sets the range of pulse widths from pulse width "MINms" to "MAXms". The setting described above is executed in rotation imaging in which, for example, abdomen is the target section.

As described above, upon setting the exposure conditions in rotation imaging and the range of pulse widths, the setting function 212 sets the exposure condition at the start of imaging (start position). That is, the setting function 212 sets tube voltage, tube current, focus size, and radiation dose to the above-noted values and sets the pulse width according to the body thickness at the start of imaging. As illustrated in FIG. 2, in rotation imaging intended for three-dimensional reconstruction, imaging is started generally from the direction close to the side direction. The setting function 212 then sets the pulse width "MINms" or "MAXms" according to the body thickness in the side direction.

Figure 8:
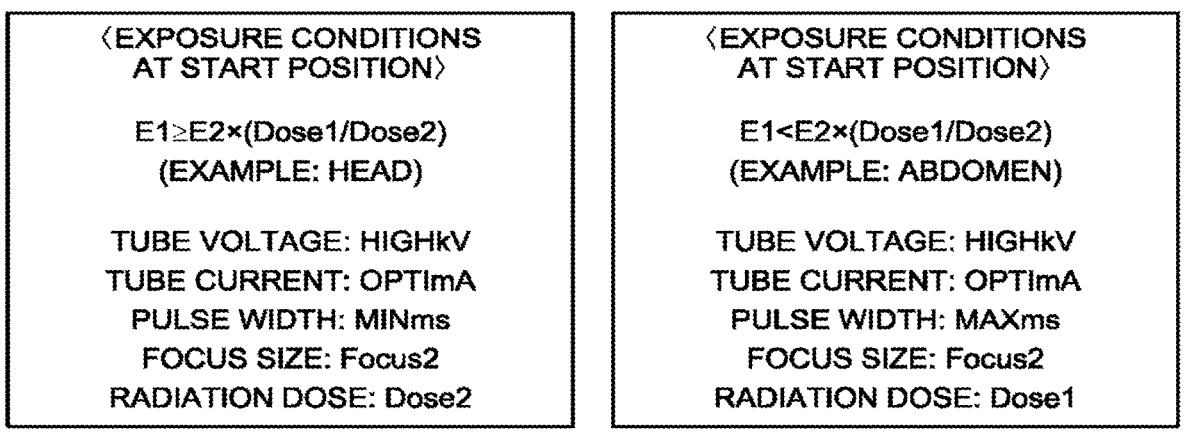
FIG. 8 is a diagram illustrating an example of the setting of exposure conditions at the start of imaging by a setting function according to the first embodiment.

FIG. 8 is a diagram illustrating an example of the setting of exposure conditions at the start of imaging by the setting function 212 according to the first embodiment. For example, when the body thickness in the side direction is thinner than in the front direction (when E1≥E2×(Dose1/Dose2)), the setting function 212 sets the pulse width to "MINms" as illustrated in the left chart in FIG. 8. For example, when head is the target section, the setting function 212 sets the pulse width at the start of imaging to "MINms".

On the other hand, when the body thickness in the side direction is thicker than in the front direction (when E1<E2×(Dose1/Dose2)), the setting function 212 sets the pulse width to "MAXms" as illustrated in the right chart in FIG. 8. For example, when abdomen is the target section, the setting function 212 sets the pulse width at the start of imaging to "MAXms". For other conditions, the values already set are used as illustrated in FIG. 8, whether E1≥E2×(Dose1/Dose2) or E1<E2×(Dose1/Dose2).

Returning to FIG. 1, the control function starts collection under the exposure conditions at the start of collection and continuously collect X-ray images by rotating the C-arm 15 while successively setting the exposure conditions within the setting range through feedback control. Specifically, the control function 213 continuously collects X-ray images by rotating the C-arm 15 while successively setting the pulse width within the range through feedback control.

For example, when the body thickness in the side direction is thinner than in the front direction (when E1≥E2×(Dose1/Dose2)), the control function 213 controls rotation imaging while successively setting the pulse width by ABC, starting from "MINms" set as the pulse width at the start of imaging. That is, when the radiation direction of X-rays changes to the front direction along with rotation, the control function 213 gradually increases the pulse width within the extent of the range "MINms to MAXms" by ABC. When the body thickness in the side direction is thicker than in the front direction (when E1<E2×(Dose1/Dose2)), the control function 213 controls rotation imaging while successively setting the pulse width by ABC, starting from "MAXms" set as the pulse width at the start of imaging. That is, when the radiation direction of X-rays changes to the front direction along with rotation, the control function 213 gradually reduces the pulse width within the extent of the range "MINms to MAXms" by ABC.

In the foregoing embodiment, tube voltage, tube current, focus size, and radiation dose are used as the exposure conditions to be set, other than pulse width. However, embodiments are not limited thereto and, for example, the additional filter, the rotational speed of the C-arm 15, the frame rate, and the like may be set. When such conditions are set, a wider range of pulse widths can be set because OLP is changed.

In the foregoing embodiment, "MINms" or "MAXms" is set as the pulse width at the start of imaging. However, embodiments are not limited thereto and, for example, the pulse width may be corrected according to the angle of the start position. As explained in FIG. 2, in the case of rotation imaging intended for three-dimensional reconstruction, rotation imaging over about 200° is performed. In this case, rotation imaging is started at a position slightly shifted from the side direction. The X-ray diagnostic apparatus 100 then corrects the pulse width according to the body thickness at the angle at the start of rotation imaging.

In such a case, the acquisition function 211 estimates the body thickness of the subject from energy "E1" in the front direction and energy "E2" in the side direction and generates an oval model representing the circumferential thickness of the subject. The setting function 212 estimates the body thickness of the subject corresponding to the angle at the start of collection of X-ray images, using the oval model, and corrects the pulse width at the start of collection. For example, the setting function 212 corrects "MINms" or "MAXms" set as the pulse width at the start of rotation imaging, according to the body thickness of the subject corresponding to the angle at the start of collection.

Figure 9:
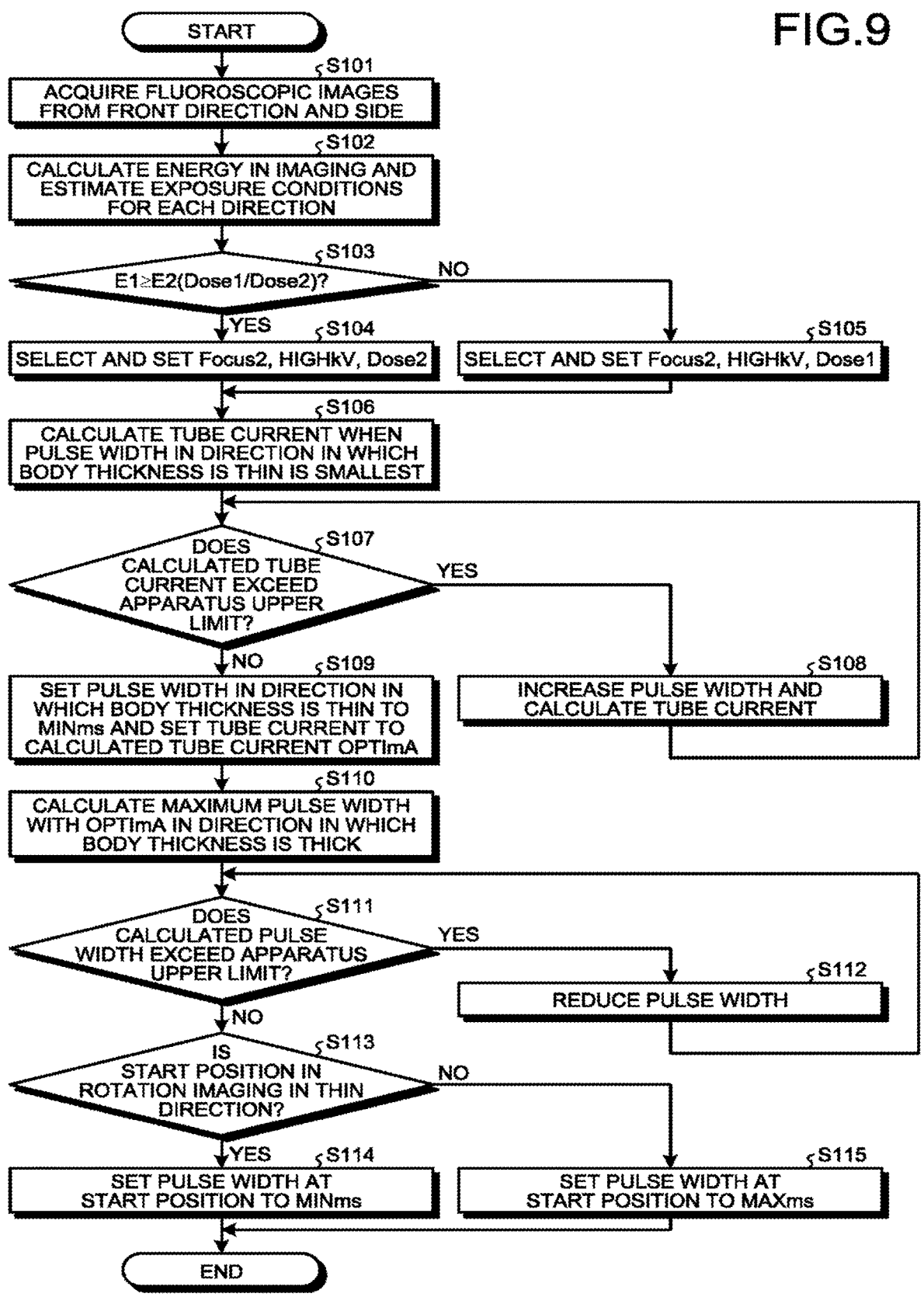
FIG. 9 is a flowchart illustrating the procedure in the X-ray diagnostic apparatus according to the first embodiment.

The processing in the X-ray diagnostic apparatus 100 according to the first embodiment will now be described with reference to FIG. 9. FIG. 9 is a flowchart illustrating the procedure in the X-ray diagnostic apparatus 100 according to the first embodiment. Steps S101 to S103 illustrated in FIG. 9 are the steps executed by the processing circuitry 21 reading, from the storage 25, and executing a computer program corresponding to the acquisition function 211. Steps S104 to S115 are the steps executed by the processing circuitry 21 reading, from the storage 25, and executing a computer program corresponding to the setting function 212.

At step S101, the processing circuitry 21 acquires fluoroscopic images from the front direction and the side direction. At step S102, the processing circuitry 21 calculates the energy at the time of imaging and estimates the exposure conditions for each direction. At step S103, the processing circuitry 21 determines whether "E1≥E2×(Dose1/Dose2)". Here, if "E1≥E2×(Dose1/Dose2)" (Yes at S103), the processing circuitry 21 selects and sets "focus size: Focus2, tube voltage: HIGHkV, radiation dose: Dose2" at step S104. On the other hand, if not "E1≥E2×(Dose1/Dose2)" (No at S103), the processing circuitry 21 selects and sets "focus size: Focus2, tube voltage: HIGHkV, radiation dose: Dose1" at step S105.

At step S106, the processing circuitry 21 calculates tube current when the pulse width in the direction in which the body thickness is thin is set to the minimum value. At step S107, the processing circuitry 21 determines whether the calculated tube current exceeds the apparatus upper limit. Here, if the calculated tube current exceeds the apparatus upper limit (Yes at S107), the processing circuitry 21 increases the pulse width, calculates tube current, and executes the determination at step S107 again, at step S108. On the other hand, if the calculated tube current does not exceed the apparatus upper limit (No at S107), the processing circuitry 21 sets the pulse width in the direction in which the body thickness is thin to "MINms" and sets the tube current to the calculated tube current "OPTImA", at step S109.

At step S110, the processing circuitry 21 calculates the maximum pulse width with tube current "OPTImA" and in the direction in which the body thickness is thick. At step S111, the processing circuitry 21 determines whether the calculated pulse width exceeds the apparatus upper limit. Here, if the calculated pulse width exceeds the apparatus upper limit (Yes at S111), the processing circuitry 21 reduces the pulse width and executes the determination at step S111 again, at step S112. On the other hand, if the calculated pulse width does not exceed the apparatus upper limit (No at S111), the processing circuitry 21 determines whether the start position in rotation imaging is in the thin direction, at step S113.

Here, if the start position in rotation imaging is in the thin direction (Yes at S113), the processing circuitry 21 sets the pulse width at the start position to "MINms", at step S114. On the other hand, if the start position in rotation imaging is not in the thin direction (No at S113), the processing circuitry 21 sets the pulse width at the start position to "MAXms", at step S115. Upon setting the pulse width at the imaging start position and the range of pulse widths "MINms to MAXms" in this manner, the processing circuitry 21 controls rotation imaging while executing ABC of the pulse width within the set range.

As described above, according to the first embodiment, the acquisition function 211 acquires body thickness information of a subject. The setting function 212 sets the exposure conditions at the start of collection of X-ray images, based on the body thickness information of the subject. The control function 213 starts collection under the exposure conditions at the start of collection and continuously collects X-ray images by rotating the C-arm 15 while successively setting the exposure conditions through feedback control. Thus, the X-ray diagnostic apparatus 100 according to the first embodiment can set the exposure conditions at the start of rotation imaging according to the body thickness of the subject, thereby improving signal to noise (S/N) and improving the image quality in rotation imaging.

According to the first embodiment, the setting function 212 further sets the range of exposure conditions of X-ray images in feedback control, based on the body thickness information of the subject. The control function 213 starts collection under the exposure conditions at the start of collection and continuously collects X-ray images by rotating the C-arm 15 while successively setting the exposure conditions within the range through feedback control. Thus, the X-ray diagnostic apparatus 100 according to the first embodiment can set the range of exposure conditions to execute feedback control within the set range, makes the setting so as to ensure the range to the maximum, and sets the optimum exposure conditions at the start of rotation imaging, thereby improving signal-to-noise (S/N) and improving the image quality in rotation imaging.

According to the first embodiment, the setting function 212 sets the range of pulse widths such that the pulse width of X-rays applied to the direction in which the body thickness of the subject is thin is reduced, and sets the pulse width included in the exposure conditions at the start of collection of X-ray images to the pulse width according to the body thickness of the subject at the start of collection. The control function 213 continuously collects X-ray images by rotating the C-arm 15 while successively setting the pulse width within the range through feedback control. Thus, the X-ray diagnostic apparatus 100 according to the first embodiment can implement feedback control more adaptive to a change in body thickness, with the range of pulse widths ensured to the maximum, thereby improving the image quality in rotation imaging.

According to the first embodiment, the setting function 212 sets the exposure conditions of X-ray images including tube voltage, tube current, focus size, and radiation dose to values according to at least one of the section to be irradiated with X-rays and the body thickness and sets the setting range of pulse widths. Thus, the X-ray diagnostic apparatus 100 according to the first embodiment enables the setting of optimum conditions even for the conditions other than pulse width.

According to the embodiment, the acquisition function 211 estimates the respective exposure conditions in imaging from two directions in which the body thickness is different, based on the exposure conditions of fluoroscopic images collected from two directions in which the body thickness is different, and acquires the body thickness information of the subject based on the estimated exposure conditions. The setting function 212 sets the exposure conditions including tube voltage, tube current, focus size, and radiation dose, based on the exposure conditions in imaging from two directions in which the body thickness is different and the body thickness information, and sets the setting range of pulse widths and the pulse width at the start of collection of X-ray images. Thus, the X-ray diagnostic apparatus 100 according to the first embodiment can set the exposure conditions using fluoroscopic images and enables the setting of more optimum conditions.

According to the first embodiment, for the focus size included in the respective exposure conditions estimated for imaging from two directions in which the body thickness is different, the setting function 212 selects and sets a focus size according to the section to be irradiated with X-rays. Thus, the X-ray diagnostic apparatus 100 according to the first embodiment enables the setting of the optimum focus size according to the section.

According to the first embodiment, the setting function 212 selects and sets a higher tube voltage in the respective exposure conditions estimated for imaging from two directions in which the body thickness is different. Thus, the X-ray diagnostic apparatus 100 according to the first embodiment can ensure a wider range of pulse widths.

According to the first embodiment, the setting function 212 selects and sets the radiation dose in the direction in which the body thickness is thin, in the respective exposure conditions estimated for imaging from two directions in which the body thickness is different. Thus, the X-ray diagnostic apparatus 100 according to the first embodiment can ensure a higher radiation dose.

According to the embodiment, the setting function 212 calculates and sets tube current such that the range of pulse widths is maximized. Thus, the X-ray diagnostic apparatus 100 according to the first embodiment is more adaptive to a change in body thickness.

According to the first embodiment, the setting function 212 sets "MAXms" or "MINms" in the range of pulse widths as the pulse width at the start of collection, according to the body thickness of the subject at the start of collection of X-ray images. Thus, the X-ray diagnostic apparatus 100 according to the first embodiment enables the appropriate setting of the pulse width at the start of rotation imaging.

According to the first embodiment, the acquisition function 211 generates an oval model representing the circumferential thickness of the subject, based on the body thickness of the subject. The setting function 212 estimates the body thickness of the subject corresponding to the angle at the start of collection of X-ray images, using the oval model, and corrects the pulse width at the start of collection. Thus, the X-ray diagnostic apparatus 100 according to the first embodiment enables more appropriate setting of the pulse width at the start of rotation imaging.

According to the first embodiment, the image processing circuitry 26 reconstructs volume data, using projection data continuously collected by rotating the C-arm 15. Thus, the X-ray diagnostic apparatus 100 according to the first embodiment can improve the image quality in rotation imaging intended for three-dimensional reconstruction.

Second Embodiment

Although the first embodiment has been described so far, a variety of different modes may be carried out in addition to the foregoing first embodiment.

Figure 10:
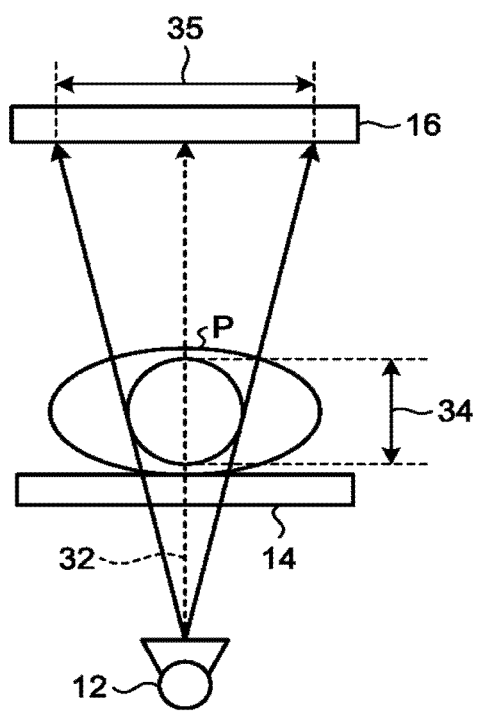
FIG. 10 is a diagram for explaining an example of estimation of body thickness according to a second embodiment.

In the foregoing first embodiment, body thicknesses in two directions are estimated, using the exposure conditions of fluoroscopic images collected in position adjustment in rotation imaging. Embodiments, however, are not limited thereto and, for example, body thickness information in two directions may be acquired from the fluoroscopic image in one direction. FIG. 10 is a diagram for explaining an example of estimation of body thickness according to a second embodiment. For example, as illustrated in FIG. 10, when a fluoroscopic image is collected from the front direction indicated by the arrow 32, the acquisition function 211 first estimates the body thickness in the front direction from attenuation of X-rays.

For example, when a fluoroscopic image of the head of the subject P is collected, the setting function 212 estimates the thickness of the head in the front direction indicated by an arrow 34, based on the attenuation of X-rays detected by the X-ray detector 16. In addition, the setting function 212 estimates the thickness of the head in the side direction (an arrow 35 in the figure), from the lateral distance of the head projected in the fluoroscopic image. The acquisition function 211 calculates energy in each direction in rotation imaging from the estimated thickness in the front direction and thickness in the side direction and estimates the exposure conditions in each direction based on the calculated energy.

In the foregoing embodiments, the body thickness is estimated based on the X-ray image (fluoroscopic image) collected by the X-ray diagnostic apparatus 100. Embodiments, however, are not limited thereto and, for example, medical images collected by other modalities may be used. In such a case, the acquisition function 211 estimates body thickness information in two directions in which the thickness of the subject is different, based on the medical images collected from the subject, and estimates the respective exposure conditions in imaging from two directions in which the thickness is different, based on the body thicknesses in the two directions. The setting function 212 sets the exposure conditions including tube voltage, tube current, focus size, and radiation dose based on the exposure conditions and the body thickness information in two directions and sets the range of pulse widths and the pulse width at the start of collection of X-ray images. For example, the acquisition function 211 acquires the body thickness information of the subject, from other medical images (for example, computed tomography (CT)) images and magnetic resonance (MR) images) collected in the past from the subject undergoing rotation imaging. The acquisition function 211 then estimates, from the acquired body thickness information, the exposure conditions in rotation imaging in two directions in which the thickness is different. The setting function 212 sets the range of pulse widths and the exposure conditions at the start of rotation imaging from the estimated exposure conditions and the body thickness.

In the foregoing embodiments, rotation imaging intended for three-dimensional reconstruction is performed. However, embodiments are not limited thereto and, for example, rotation imaging intended for 3D-digital subtraction angiography (DSA) reconstruction may be performed. In such a case, in collection of 3D-DSA images, the control function 213 continuously collects mask images by rotating the C-arm 15 while successively setting the exposure conditions within the range through feedback control and collects contrast images while executing the control identical to the feedback control in collecting mask images.

In generation of 3D-DSA images, rotation imaging is executed before and after injection of contrast medium. That is, mask images are collected through rotation imaging before contrast medium is injected, and contrast images are collected through rotation imaging after contrast medium is injected. Then, in the X-ray diagnostic apparatus 100 according to the second embodiment, the ABC of pulse width described above is executed at the time of collection of mask images, and the control identical to the control at the time of mask image collection is executed at the time of collection of contrast images. That is, the control function 213 performs control such that the mask images and the contrast images collected in the identical direction during rotation imaging are collected under the same conditions (same pulse width). This control improves the S/N of the collected mask images and contrast images and standardizes the imaging sequence to improve the image quality of collected 3D-DSA images.

In collection of 3D-DSA images, the body thickness of the subject is estimated from the exposure conditions of fluoroscopic images in two directions to generate an oval model representing the circumferential body thickness, and the pulse width fit for the generated oval model is set in each direction, thereby matching the imaging sequence of mask images with the imaging sequence of contrast images. For example, the imaging sequences can be standardized by creating a table in which the pulse width fit for the oval model is set in each direction, and executing the imaging sequence of both images in accordance with the created table. However, the circumferential body thickness is unable to be estimated accurately from the fluoroscopic images in two directions, and the error is significant. By contrast, according to the foregoing embodiments, since information of a change in pulse width that follows the body thickness is acquired by ABC, the imaging sequence is matched accordingly to enable imaging with higher accuracy.

Fluoroscopy performed in three or more directions (all directions at maximum) can improve the accuracy of estimation of body thickness but leads to increase in exposure and increase operation. The foregoing embodiment estimates the body thickness of the subject based on fluoroscopic images collected from two directions to execute ABC and thereby enables rotation imaging under highly accurate exposure conditions fit for the shape (body thickness) of the subject while suppressing exposure and operation.

In the foregoing embodiments, the pulse width of X-rays to be applied is successively set according to a change in body thickness of the subject. Embodiments, however, are not limited thereto and, for example, tube current may be successively set according to a change in body thickness of the subject. In such a case, for example, the setting function 212 sets tube current at the start of collection of X-ray images, based on the body thickness information of the subject. The control function 213 then executes feedback control of tube current by ABC during rotation imaging.

The components of the devices illustrated in the first embodiment are functional and conceptual and are not necessarily physically configured as illustrated in the figures. That is, the specific manner of distribution or integration of the devices is not limited to the manner illustrated in the figures, and the devices may be entirely or partially distributed and/or integrated functionally or physically in desired units depending on various loads and use conditions. The whole or any part of the processing function performed in each device may be implemented by a CPU and a computer program analyzed and executed in the CPU or may be implemented in the form of hardware with wired logic.

The control method described in the foregoing embodiments may be implemented by a control program prepared in advance and executed by a computer such as a personal computer and a workstation. The display program can be distributed over a network such as the Internet. The control program may be recorded on a computer-readable recording medium such as hard disk, flexible disk (ED), compact disc read-only memory (CD-ROM), magheto-optical disk (MO), and digital versatile disc (DVD) and may be read from the recording medium by a computer for execution.

As described above, according at least one embodiment, the image quality in rotation imaging can be improved.

While certain embodiment save been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:
an X-ray tube configured to radiate X-rays;
an X-ray detector configured to detect the X-rays;
an arm holding the X-ray tube; and
processing circuitry configured to;
obtain two acquisition conditions for X-ray images acquired from two acquisition directions with different body thicknesses,
compare sizes of the two body thicknesses corresponding to the two acquisition conditions to determine whether a direction at a start of acquisition of a plurality of X-ray images corresponds to a thicker one or a thinner one of the two body thicknesses,
set, based on the two acquisition conditions and the determined one of the two body thicknesses corresponding to the direction at the start of acquisition, a start condition corresponding to the start of acquisition of the plurality of X-ray images,
begin acquiring of the plurality of X-ray images with the start condition, and
acquire the plurality of X-ray images sequentially by rotating the arm around one part of a circumference of a subject while iteratively setting acquisition conditions for acquiring of the plurality of X-ray images by feedback control, the feedback control comprising sequentially adjusting the acquisition conditions based on a comparison result between a threshold and a pixel value in one of the plurality of X-ray images sequentially acquired by rotating the arm, wherein
the processing circuitry is configured to set the start condition corresponding to the start of acquisition of the plurality of X-ray images for keeping a change in pulse width within a preset pulse width range, the pulse width being iteratively set by the feedback control.

2. The X-ray diagnosis apparatus according to claim 1, wherein
the processing circuitry is configured to obtain the two acquisition conditions based on fluoroscopic images acquired from a plurality of acquisition directions with different body thicknesses.

3. The X-ray diagnosis apparatus according to claim 2, wherein
the processing circuitry is further configured to:
set a range of the acquisition conditions set by the feedback control,
begin acquiring of the plurality of X-ray images with the start condition, and
acquire the plurality of X-ray images sequentially by rotating the arm while iteratively setting the acquisition conditions within the range by the feedback control.

4. The X-ray diagnosis apparatus according to claim 3, wherein
the processing circuitry is configured to:
set a range of a pulse width so that the pulse width of the X-rays to be irradiated in a direction in which the body thickness is thin becomes narrow,
set a pulse width corresponding to the body thickness at the start of acquisition of the plurality of X-ray images, as a pulse width at the start of acquisition of the plurality of X-ray images, and
acquire the plurality of X-ray images sequentially by rotating the arm while iteratively setting the pulse width within the range by the feedback control.

5. The X-ray diagnosis apparatus according to claim 4, wherein
the processing circuitry is further configured to set, in accordance with at least one of a site to be irradiated with the X-rays and body thickness, the start condition including a tube voltage, a tube current, a focal spot size and a radiation dose, and set the range of the pulse width.

6. The X-ray diagnosis apparatus according to claim 5, wherein
the processing circuitry is configured to:
determine two estimated acquisition conditions for the acquisition of X-ray images from two acquisition directions with different body thicknesses based on two fluoroscopic conditions of two fluoroscopic images acquired from the two acquisition directions,
obtain body thickness information of the subject based on the estimated two acquisition conditions, and
set, based on the two estimated acquisition conditions and the obtained body thickness information, the start condition including the tube voltage, the tube current, the focal spot size and the radiation dose, the range of the pulse width and the pulse width at the start of acquisition of the plurality of X-ray images.

7. The X-ray diagnosis apparatus according to claim 6, wherein
the processing circuitry is configured to set the focal spot size by selecting a focal spot size corresponding to the site to be irradiated with the X-rays, from two focal spot sizes included in the two estimated acquisition conditions in acquiring the X-ray images from the two acquisition directions.

8. The X-ray diagnosis apparatus according to claim 6, wherein
the processing circuitry is configured to set the tube voltage by selecting a higher tube voltage, from two tube voltages included in the two estimated acquisition conditions in acquiring the X-ray images from the two acquisition directions.

9. The X-ray diagnosis apparatus according to claim 8, wherein
the processing circuitry is configured to set the radiation dose by selecting a radiation dose corresponding to the direction in which the body thickness is thin, from two radiation doses included in the two estimated acquisition conditions in acquiring the X-ray images from the two acquisition directions.

10. The X-ray diagnosis apparatus according to claim 6, wherein
the processing circuitry is configured to calculate and set the tube current so that the range of the pulse width becomes a maximum wide range.

11. The X-ray diagnosis apparatus according to claim 6, wherein
the processing circuitry is configured to set, as the pulse width at the start of acquisition of the plurality of X-ray images, a maximum value or a minimum value in the range of the pulse width based on the body thickness at the start of acquisition of the plurality of X-ray images.

12. The X-ray diagnosis apparatus according to claim 11, wherein
the processing circuitry is further configured to;
generate an elliptical model indicating thickness in a circumferential direction of the subject according to the body thickness of the subject,
estimate a body thickness of the subject corresponding to an angle at the start of acquisition of the plurality of X-ray images, by using the elliptical model, and
correct the pulse width at the start of acquisition of the plurality of X-ray images.

13. The X-ray diagnosis apparatus according to claim 1, further comprising:
reconstruction circuitry configured to reconstruct a volume data using projection data sequentially acquired by rotating the arm.

14. The X-ray diagnosis apparatus according to claim 13, wherein
the processing circuitry is further configured to acquire mask images sequentially by rotating the arm while iteratively setting the acquisition conditions within the range by the feedback control and acquire contrast images by the same control as the feedback control executed at the time of acquiring the mask images, in acquiring 3D digital subtraction angiography (DSA) images.

15. The X-ray diagnosis apparatus according to claim 5, wherein
the processing circuitry is configured to;
estimate two body thickness information in acquisition directions with different thicknesses based on medical images acquired from the subject,
determine two estimated acquisition conditions in acquiring the X-ray images from the acquisition directions based on the body thickness information in the two acquisition directions, set, based on the two estimated acquisition conditions and the body thickness information in the two acquisition directions, the start condition including the tube voltage, the tube current, the focal spot size and the radiation dose, the range of the pulse width and the pulse width corresponding to the start of acquisition of the plurality of X-ray images.

16. The X-ray diagnosis apparatus according to claim 1, wherein the processing circuitry is configured to set the start condition by setting the acquisition condition at the start of acquisition of the plurality of X-ray images for keeping (a) a first pulse width of an X-ray irradiated in a direction of the thinner one of the body thicknesses above a lower limit of a preset pulse width range and (b) a second pulse width of an X-ray irradiated in a direction of the thicker one of the body thicknesses below an upper limit of the preset pulse width range.

17. An X-ray diagnosis apparatus, comprising:
an X-ray tube configured to radiate X-rays;
an X-ray detector configured to detect the X-rays;
an arm holding the X-ray tube; and
processing circuitry configured to;
obtain two acquisition conditions for X-ray images acquired from two acquisition directions with different body thicknesses,
compare sizes of the two body thicknesses corresponding to the two acquisition conditions to determine whether a direction at a start of acquisition of a plurality of X-ray images corresponds to a thicker one or a thinner one out of the two body thicknesses,
set, in accordance with the two acquisition conditions and the determined one of the two body thicknesses corresponding to the direction at the start of acquisition, a start pulse width corresponding to the start of acquisition of the plurality of X-ray images,
begin acquiring of the plurality of X-ray images with the start pulse width, and
acquire the plurality of X-ray images sequentially by rotating the arm around one part of a circumference of a subject while iteratively setting the acquisition pulse widths for acquiring of the plurality of X-ray images by feedback control, the feedback control comprising sequentially adjusting the acquisition pulse widths based on a comparison result between a threshold and a pixel value in one of the plurality of X-ray images sequentially acquired by rotating the arm, wherein
the processing circuitry is further configured to set the start pulse width corresponding to the start of acquisition of the plurality of X-ray images for keeping a change in pulse width within a preset pulse width range, the pulse width being iteratively set by the feedback control.

18. The X-ray diagnosis apparatus according to claim 17, wherein the processing circuitry is configured to set the start condition by setting the acquisition condition at the start of acquisition of the plurality of X-ray images for keeping (a) a first pulse width of an X-ray irradiated in a direction of the thinner one of the body thicknesses above a lower limit of a preset pulse width range and (b) a second pulse width of an X-ray irradiated in a direction of the thicker one of the body thicknesses below an upper limit of the preset pulse width range.

19. A control method executed by an apparatus, comprising:
obtaining two acquisition conditions for X-ray images acquired from two acquisition directions with different body thicknesses;

comparing sizes of the two body thicknesses corresponding to the two acquisition conditions to determine whether a direction at a start of acquisition of a plurality of X-ray images corresponds to thicker one or thinner one out of the two body thicknesses, setting, based on the two acquisition conditions and the determined one of the two body thicknesses corresponding to the direction at the start of acquisition, a start condition corresponding to the start of acquisition of the plurality of X-ray images;

beginning acquiring of the plurality of X-ray images with the start condition; and acquiring the plurality of X-ray images sequentially by rotating an arm around one part of a circumference of a subject while iteratively setting acquisition conditions for acquiring of the plurality of X-ray images by feedback control, the feedback control comprising sequentially adjusting the acquisition conditions based on a comparison result between a threshold and a pixel value in one of the plurality of X-ray images sequentially acquired by rotating the arm, wherein setting the start condition corresponding to the start of acquisition of the plurality of X-ray images for keeping a change in pulse width within a preset pulse width range, the pulse width being iteratively set by the feedback control.

20. The control method to claim 19, comprising setting the start condition by setting the acquisition condition at the start of acquisition of the plurality of X-ray images for keeping (a) a first pulse width of an X-ray irradiated in a direction of thin the thinner one of the body thicknesses above a lower limit of a preset pulse width range and (b) a second pulse width of an X-ray irradiated in a direction of the thicker one of the body thicknesses below an upper limit of the preset pulse width range.

* * * * *